United States Patent
Berg et al.

(10) Patent No.: US 6,545,027 B1
(45) Date of Patent: Apr. 8, 2003

(54) METHODS OF MODULATING NF-KB TRANSCRIPTION FACTOR

(75) Inventors: David T. Berg, Beech Grove, IN (US); David S. Calnek, Indianapolis, IN (US); Brian W. Grinnell, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/474,936

(22) Filed: Jun. 7, 1995

(51) Int. Cl.[7] .................. A61K 31/44; A61K 31/38; A61K 31/27

(52) U.S. Cl. .................. 514/347; 514/333; 514/443; 514/483

(58) Field of Search .................. 514/443, 483, 514/910, 317, 333, 347

(56) References Cited

U.S. PATENT DOCUMENTS

| | | | |
|---|---|---|---|
| 4,133,814 A | 1/1979 | Jones et al. | 260/326.55 |
| 4,380,635 A | 4/1983 | Peters | 546/202 |
| 4,418,068 A | 11/1983 | Jones | 424/267 |
| 5,075,321 A | 12/1991 | Schreiber | 514/317 |
| 5,393,763 A | 2/1995 | Black et al. | 514/333 |
| 6,410,516 B1 | 6/2002 | Baltimore et al. | 514/44 |

FOREIGN PATENT DOCUMENTS

| | | |
|---|---|---|
| EP | 652003 | 5/1995 |
| EP | 659427 | 6/1995 |
| EP | 664121 | 7/1995 |
| EP | 664126 | 7/1995 |
| EP | 668075 | 8/1995 |
| WO | WO 9612491 | 5/1996 |

OTHER PUBLICATIONS

Levenson et al., "Transfection of human estrogen receptor (ER) cDNA into ER–negative mammalian cell lines", J. Steroid Biochem. Mol. Biol., vol. 51, No. 5–6, 1994 (pp. 229–239).
Yang et al., "Raloxifene, an antiestrogen, stimulates the effects of estrogen on inhibiting bone resorption through regulating TGF–beta–3 expression in bone", Journal of Bone and Mineral Research, vol. 8, No. s1, Aug., 1993, (p. s118).
Galien et al., "Involvement of CCAAT/enhancer–binding protein and nuclear factor kappaB binding sites in interleukin–6 promoter inhibition by estrogens", Molecular Endocrinology, vol. 10, No. 6, Jun., 1996 (pp. 713–722).
Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyroid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;". Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.

(List continued on next page.)

*Primary Examiner*—Theodore J. Criares
(74) *Attorney, Agent, or Firm*—William R. Boudreaux; James J. Sales

(57) ABSTRACT

A method of modulating NF-kB transcription factor comprising administering to a human in need thereof an effective amount of a compound having the formula

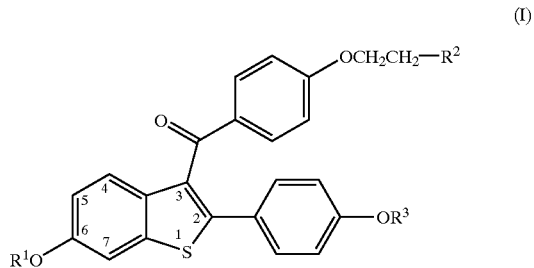

wherein
R[1] and R[3] are independently hydrogen,

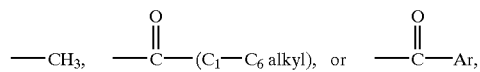

wherein Ar is optionally substituted phenyl;
R[2] is selected from the group consisting of pyrrolidine, hexamethyleneamino, and piperidino; or a pharmaceutically acceptable salt of solvate thereof.

2 Claims, No Drawings

OTHER PUBLICATIONS

Black et al., "Uterine Bioassay of Tamoxifen, Trioxifene, and New Estrogen Antagonist (LY1170118) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L.J. "Biological Actions and Binding Properties of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2 (4–methoxyphenyl)–l–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF MODULATING NF-KB TRANSCRIPTION FACTOR

BACKGROUND OF THE INVENTION

The control of all biological processes results from a balance between various positive and negative-acting factors which interact with DNA regulatory elements and with each other. These protein factors play a critical role in controlling the expression of proteins, and thus are critical to both normal and pathological processes. Understanding these protein factors and how they modulate gene expression is key to strategies for the development of agents to control disease initiation and progression.

A number of these important trans-acting regulatory proteins have been described in the literature and have been demonstrated to play a role in pathological processes. One such factor is NF-kB, a member of the Rel family of eukaryotic transcription factors. The Rel family of proteins controls a wide variety of cellular responses. For example, they are key regulatory molecules for signal-responsive induction of gene expression, host-defensive responses, and growth responses. The ability to specifically modulate the binding of NF-kB and other members of the Rel family would be useful for the treatment of a wide variety of conditions ranging from septic shock, graft vs host reactions, acute inflammatory conditions, systemic inflammatory responses, acute phase responses, vascular coagulation, ischemic reperfusion injury, atherosclerosis, HIV infection and cancer.

Another transcription factor of importance is BEF-1, a member of the NF-1 family of transcriptional regulators. BEF-1 was first identified as a transcriptional repressor within the enhancer of human BK virus. The binding site for this ubiquitous transcription factor is present in the regulatory regions of a number of human genes. For example, BEF-1 has been shown to control the expression of human apolipoprotein E, a major constituent of plasma lipoprotein that functions in lipid transport and redistribution (reverse cholesterol transport). ApoE also probably plays an important role in inhibiting the development and/or progression of atherosclerosis. Both the level and binding activity of BEF-1 have been shown to be regulated via intracellular signaling, as demonstrated by effects mediated through the viral oncogene Ela, cytokines and also through tyrosine phosphorylation.

We have found that BEF-1 binding sites can overlap with NF-kB binding sites (e.g.., vascular adhesion molecule-1: VCAM-1). Conversely, BEF-1 binding sites such as in the apoE promoter can bind Rel proteins. Thus, both BEF-1 and NF-kB may compete for binding at the same site. Furthermore, compounds that modulate the levels of BEF-1 activity may be effective not only in modulating genes controlled by BEF-1, but those controlled by NF-kB as well.

SUMMARY OF THE INVENTION

This invention provides methods for modulating NF-kB transcription factor comprising administering to a human in need thereof an effective amount of a compound of formula I

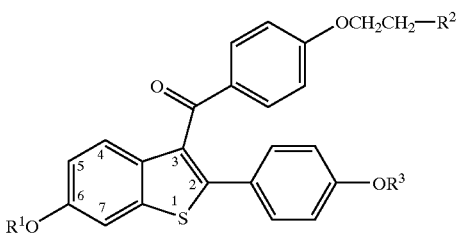

(I)

wherein $R^1$ and $R^3$ are independently hydrogen,

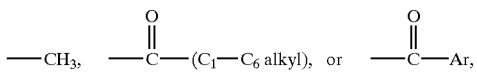

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for modulating NF-kB transcription factor.

The methods of use provided by this invention are practiced by administering to a human in need thereof a dose of a compound of formula I or a pharmaceutically acceptable salt or solvate thereof, that is effective to modulate NF-kB transcription factor. As such, the present method includes both medical therapeutic and/or prophylactic administration, as appropriate.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1-C_6$ alkyl, $C_1-C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to modulate NF-kB transcription factor, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively modulate NF-kB transcription factor, or any other use disclosed herein.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Treatment of Cells with Compound A*

Human HepG2 cells were cultured in 3:1 v/v mixture of Dulbecco's modified Eagle's medium and Ham's nutrient mixture F12, supplemented with 10 nM selenium, 50 uM 2 amino ethanol, 20 mM HEPES and 50 ug/ml gentamycin and 2.5% fetal bovine serum. When cells reached confluence, the monolayers were rinsed once with HBSS and fed with the above medium without FBS, but with 100 ug/ml fatty-acid free BSA, 0.8 ug/ml oleic acid, and with or without the addition of 10 nM compound A. After incubation for 24 hours, cells were processed for nuclear extracts, and nuclear factor assays were performed as described below and by Reifel-Miller et al. (Reifel-Miller, A. E., Berg, D. T. and Grinnell, B. G. (1991) *The Journal of Biological Chemistry* 266, 13873–13882).

Nuclear Factor Binding by Gel Mobility Retardation Assay—

Nuclear extracts were prepared as described by Dignam, J. D., Lebovitz, R. M. and Roeder, R. G. (1983) *Nucleic Acids Res.* 11, 1475–1489 For the Gel Mobility Retardation Assay the nuclear factor binding site for NF-kB was from VCAM-1 5'-CCTTGAAGGGATTTCCCTCCGCCT-3 and for BEF-1 was the prototype sequence 5'-AGTGCATGACTGGGCAGCCAGCCAGTGGCAG-3'. The oligonucleotides were labeled at their 5' ends with T4 polynucleotide kinase (Bethesda Research Laboratories, Inc.) and (g-$^{32}$P) ATP (Du Pont-New England Nuclear).

Either nuclear extracts containing BEF-1 or the purified human NF-kB proteins (p49 and p50) were incubated with 0.2–0.3 pmol of probe (approximately 10,000 cpm) at 25° C. for 30 min. The 10-ul reaction mixture also contained 200 ng of poly (dI-dC)—poly (dI-dC) (Pharmacia), 15% glycerol, 20 mM HEPES (pH 7.9), 100 mM KCl, 5 mM $MgCl_2$, 0.2 mM EDTA, and 0.5 mM dithiothreitol. Following the 30 minute incubation, samples were subjected to electrophoresis on a 4% low ionic strength polyacrylamide gel as described by Fried, M. and Crothers, D. M. (1981) *Nucleic Acids Res.* 9, 6505–6525. After the gel was dried, the specific protein-DNA complexes were visualized by autoradiography and quantitated using a Betascope 603 Blot Analyzer or phosphoimager (Molecular Dynamics). The results from quantitation with the use of a Betascope 603 Blot Analyzer are expressed as the amount of labeled probe bound/amount of probe free per ug of protein. The data from the phosphoimager was analyzed with TP Label gel software (Ver 1.5, Signal Analytics Corp.) and are expressed as pixel intensity units (PU).

Results

Using the transcription factor binding assays, we assessed the ability of BEF-1 present in cell extracts to bind to the VCAM NF-kB binding site and conversely for purified NF-kB p49 and p50 to bind to the BEF-1 binding site. As shown in Table 1 using two levels of BEF-1 containing nuclear extract, we obtained a concentration-dependent binding of BEF-1 to the VCAM-1 NF-kB binding site. As shown in Table 2, purified NF-kB proteins (p50 and p49: Promega) bound to the prototype BEF-1 binding site in a concentration-dependent manner. As would be expected these two NF-kB proteins also bound to the VCAM NF-kB binding site.

The effect of compound A on the level of intracellular BEF-1 was determined by measuring the BEF-1 binding activity in nuclear extracts prepared from compound A —treated and untreated human HepG2 cells. As shown in Table 3, in four separate experiments the treatment of cells with 10 nM compound A resulted in a 193 to 293% (mean of 253+/−42 increase in the level BEF-1. Thus, compound A increases the levels of the intracellular repressor BEF-1, and thus can modulate the activity of genes controlled by BEF-1. Further, the ability of BEF-1 to interact at NF-kB binding sites, indicates that compound A could be effective in blocking the action of the important cellular regulatory molecule NF-kB.

TABLE 1

Binding of BEF-1 to an NF-kB binding site

| BEF-1 containing Nuclear Extract | Binding Site | BEF-1/Binding Site Complex (PIU) |
| --- | --- | --- |
| None. | VCAM1 (NF-kB) | 0 |
| 1.4 ug | VCAM1 (NF-kB) | 8.63 |
| 2.8 ug | VCAM1 (NF-kB) | 15.03 |

TABLE 2

Binding of purified NF-kB to the BEF-1 and NF-kB binding sites.

| NF-kB proteins | Binding Site | NF-kB/Binding Site Complex (PIU) |
| --- | --- | --- |
| None. | BEF-1 | 0.88 |
| p50 56 pg | BEF-1 | 4.46 |
| p50 112 pg | BEF-1 | 11.16 |
| p49 74 pg | BEF-1 | 42.66 |
| p49 148 pg | BEF-1 | 77.73 |
| None | VCAM1 (NF-kB) | −0.04 |
| P50 112 pg | VCAM1 (NF-kB) | 46.19 |
| P49 148 pg | VCAM1 (NF-kB) | 17.02 |

TABLE 3

The effect of compound A on the level of intracellular BEF-1

| Experiment Number | Compound A Treatment | Binding Activity (bound/free per ug) | Percent Change with Treatment |
| --- | --- | --- | --- |
| 1 | − | 0.12 | |
|   | + | 0.33 | 292 |
| 2 | − | 0.14 | |
|   | + | 0.27 | 195 |
| 3 | − | 0.12 | |
|   | + | 0.33 | 275 |
| 4 | − | 0.12 | |
|   | + | 0.30 | 250 |

*Compound A is of the formula I wherein $R_1$ and $R_3$ are hydroxy, and $R_2$ is pyrrolidino.

We claim:

1. A method of modulating NF-kB transcription factor comprising administering to a human in need thereof an effective amount of a compound having the formula

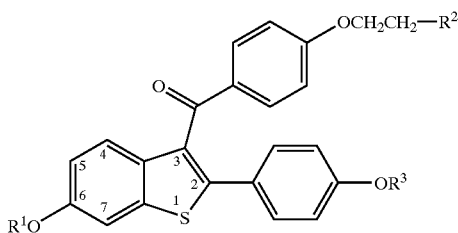

(I)

wherein

R[1] and R[3] are independently hydrogen,

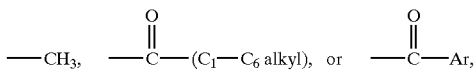

wherein Ar is optionally substituted phenyl;

R[2] is selected from the group consisting of pyrrolidine, hexamethylenemino, and piperidino; or a pharmaceutically acceptable salt of solvate thereof.

2. The method of claim 1 wherein said compound is the hydrochloride salt thereof.

* * * * *

UNITED STATES PATENT AND TRADEMARK OFFICE
CERTIFICATE OF CORRECTION

PATENT NO.  : 6,545,027 B1
DATED       : April 8, 2003
INVENTOR(S) : Berg et al.

It is certified that error appears in the above-identified patent and that said Letters Patent is hereby corrected as shown below:

<u>Column 9, lines 25-40 and Column 10, lines 24-36,</u>
Claim 1 should read as follows:

1. A method of treating HIV infection by modulating NF-κB transcription factor comprising administering to a human in need thereof an effective amount of a compound having the structure:

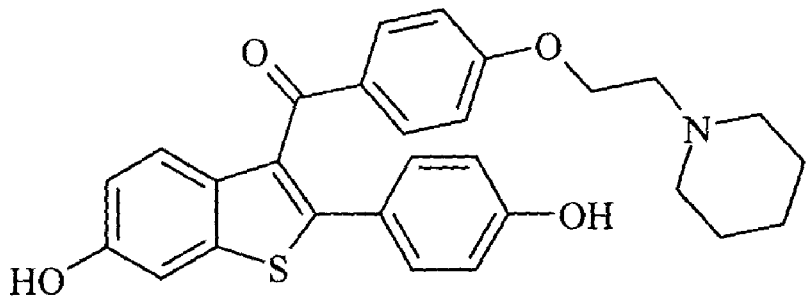

or its hydrochloride salt.

Signed and Sealed this

Second Day of September, 2003

JAMES E. ROGAN
*Director of the United States Patent and Trademark Office*

Disclaimer

6,545,027 B1—David T. Berg, Beech Grove, IN (US); David S. Calnek, Indianapolis, IN (US); Brian W. Grinnell, Indianapolis, IN (US). METHODS OF MODULATING NF-KB TRANSCRIPTION FACTOR. Patent dated Apr. 8, 2003. Disclaimer filed Jun. 25, 2004, by the assignee, Eli Lilly and Company.

Hereby enters this disclaimer to all claims of said patent.

*(Official Gazette, August 17, 2004)*

SEQUENCE LISTING

<160> NUMBER OF SEQ ID NOS: 2

<210> SEQ ID NO 1
<211> LENGTH: 24
<212> TYPE: PRT
<213> ORGANISM: Homo sapiens

```
<400> SEQUENCE: 1

Cys Cys Thr Thr Gly Ala Ala Gly Gly Ala Thr Thr Thr Cys Cys
1               5                   10                  15

Cys Thr Cys Cys Gly Cys Cys Thr
                20

<210> SEQ ID NO 2
<211> LENGTH: 31
<212> TYPE: PRT
<213> ORGANISM: Homo sapiens

<400> SEQUENCE: 2

Ala Gly Thr Gly Cys Ala Thr Gly Ala Cys Thr Gly Gly Cys Ala
1               5                   10                  15

Gly Cys Cys Ala Gly Cys Cys Ala Gly Thr Gly Gly Cys Ala Gly
                20                  25                  30
```